United States Patent
Bales et al.

(10) Patent No.: US 6,579,301 B1
(45) Date of Patent: Jun. 17, 2003

(54) INTRAGASTRIC BALLOON DEVICE ADAPTED TO BE REPEATEDLY VARIED IN VOLUME WITHOUT EXTERNAL ASSISTANCE

(75) Inventors: Thomas O. Bales, Coral Gables, FL (US); Kevin W. Smith, Coral Gables, FL (US)

(73) Assignee: Syntheon, LLC, Miami, FL (US)

(*) Notice: Subject to any disclaimer, the term of this patent is extended or adjusted under 35 U.S.C. 154(b) by 137 days.

(21) Appl. No.: 09/716,008

(22) Filed: Nov. 17, 2000

(51) Int. Cl.[7] .............................................. A61M 29/02
(52) U.S. Cl. ...................... 606/191; 606/192; 606/195; 604/96.01; 604/97.01; 604/99.01
(58) Field of Search ..................... 604/96.01, 97.01, 604/97.03, 98.01, 99.01, 99.02, 99.03, 99.04, 103.11; 606/191, 192, 195

(56) References Cited

U.S. PATENT DOCUMENTS

| 4,133,315 A | | 1/1979 | Berman |
| 4,517,979 A | | 5/1985 | Pecenka |
| 4,813,934 A | | 3/1989 | Engelson |
| 4,899,747 A | | 2/1990 | Garren |
| 4,925,446 A | * | 5/1990 | Garay et al. ................ 128/899 |
| 5,084,061 A | | 1/1992 | Gau et al. |
| 5,129,915 A | * | 7/1992 | Cantenys ..................... 128/898 |
| 5,234,454 A | | 8/1993 | Bangs |
| 5,259,399 A | | 11/1993 | Brown |
| 5,308,326 A | | 5/1994 | Zimmon |

FOREIGN PATENT DOCUMENTS

WO    WO 87/00034    * 1/1987

* cited by examiner

*Primary Examiner*—John J. Calvert
*Assistant Examiner*—Shaun R Hurley
(74) *Attorney, Agent, or Firm*—Gordon & Jacobson P.C.

(57) ABSTRACT

An intragastric balloon device includes a flexible bladder, a relatively rigid reservoir coupled to the bladder and adapted to hold a bladder inflation fluid, and an inflation/deflation system adapted to move or permit movement of the fluid from the reservoir and into the bladder. The intragastric balloon device is sized such that it may be positioned, in its entirety, into the stomach cavity. Various systems may be used to move or permit movement of the fluid. A control system is provided to automatically activate the inflation/deflation system. The automatic activation may be activated by a combination of one or more of a timer, the temperature of the stomach, the pressure in the stomach, the mechanical stress in the stomach, or another sensed condition, at which the control system is programmed or otherwise configured to activate.

21 Claims, 4 Drawing Sheets

INTRAGASTRIC BALLOON DEVICE ADAPTED TO BE REPEATEDLY VARIED IN VOLUME WITHOUT EXTERNAL ASSISTANCE

BACKGROUND OF THE INVENTION

1. Field of the Invention

This invention relates broadly to medical devices. More particularly, this invention relates to gastric balloons.

2. State of the Art

In the treatment of obesity, gastric balloons have been inserted into the stomach to assume a portion of the volume of the stomach cavity, and reduce the available capacity of the stomach for food. This has the effect of reducing the appetite and, consequently, over time, e.g., three months, and in combination with a suitable diet, causes weight loss. However, when provided with a balloon of relatively constant volume over the treatment time, in many cases the stomach expands to accommodate the balloon ('balloon accommodation') and recovers a portion or all of its former capacity for food intake, thereby defeating the purpose of the balloon and reducing the effectiveness of the treatment.

A number of gastric balloon systems have been invented which permit the volume of a gastric balloon to be varied over time. The purpose of the facilitating volumetric change in the gastric balloon has been to provide periods of feelings of relief and well-being to the patient, not to prevent balloon accommodation and maintain appetite reduction. One system, disclosed in U.S. Pat. No. 4,133,315 to Berman, utilizes a flexible filling/release tube permanently coupled to the balloon and which in one embodiment extends from the balloon, through the esophagus, and out the nasal pathway or mouth. In another embodiment, the tube extends surgically through the stomach wall and through the wall of the abdomen. Fluid can be pressurized into the balloon through the tube to cause balloon expansion, or released or evacuated from the tube to permit the balloon collapse, thereby varying the volume of the balloon. A similar implanted tube system is described in U.S. Pat. No. 5,234,454 to Bangs. However, for several reasons, the Berman and Bangs systems are not particularly desirable. First, the tube can cause irritation and even infection of tissue, particularly of the esophagus in the Berman system. Second, the tube can cause discomfort, at times severe, to the patient. Third, the implanted balloon tube requires that the patient be subject to a surgical incision.

In other systems, for example the system disclosed in U.S. Pat. No. 5,084,061 to Gau, a free floating gastric balloon is provided with a valve which can be detachably coupled to a filling tube. When it is desired to add or relieve pressure to the balloon, the filling tube is endoscopically extended into the stomach and coupled to the balloon. Fluid is then passed into or withdrawn from the balloon. While this system eliminates the issue of having a filling tube extend out of the body for the duration of the treatment, pressure changes to the balloon must be performed under a physician's care and under sedation. As such, the balloon is not adaptable to change in size multiple times per day, e.g., after meals and, as such, cannot satisfactorily prevent balloon accommodation.

U.S. Pat. No. 5,259,399 to Brown discloses a system in which a balloon or bladder inserted in the stomach is controllably filled and emptied using a filling system which extends through a gastrostomy tube implanted between the stomach and the abdomen of the body and terminates outside the body. The filling system includes a reversible pump and a two-way valve connected to a filling tube. In addition, an electronic control is provided for operating the filling system and altering the size of the bladder according to a schedule or according to a set of physiological conditions of the body monitored by filling system. While this ability to vary the volume of the bladder according to a schedule or upon meeting physiological conditions is quite desirable to prevent balloon accommodation, the system has several drawbacks. First, the filling system is inserted by "implantation" which requires an initial surgical procedure. In addition, extending the system through the abdomen may lead to infection. Furthermore, the external location of portions of the filling system may subject the system to unintended physical impact, resulting in physical trauma to the patient.

SUMMARY OF THE INVENTION

It is therefore an object of the invention to provide an intragastric balloon device which is adapted to be entirely located within the stomach cavity.

It is another object of the invention to provide an intragastric balloon device adapted to vary in volume without a control means which is external and mechanically connected to the balloon device.

In accord with these objects, which will be discussed in detail below, an intragastric balloon device is provided and includes a flexible bladder, a relatively rigid reservoir coupled to the bladder and adapted to hold a bladder inflation fluid, and an inflation/deflation system adapted to move or permit movement of the fluid from the reservoir and into the bladder. The intragastric balloon device is sized such that it may be inserted, in its entirety, into the stomach through the esophagus.

According to the invention, various systems may be used to move or permit movement of the fluid. In several embodiments, the system is a pump which moves the fluid between the reservoir and the bladder. In other embodiments, the system includes a mechanism for heating a fluid to cause the heated fluid to expand the bladder. According to other embodiments, no reservoir is employed and a pump pumps stomach fluid into the bladder to inflate the bladder.

According to a preferred aspect of the invention, the intragastric balloon device also includes a control system which is adapted to automatically activate the inflation/deflation system. The automatic activation may be activated by a combination of one or more of a timer, a temperature of the stomach, a pressure in the stomach, a mechanical stress in the stomach, or another sensed condition, at which the control system is programmed or otherwise configured to activate. The control system is preferably reprogrammable or instantly operable via an external transmitter. In addition, the control system and the pump, where utilized, are preferably battery-powered such that the intragastric balloon device is self-contained.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
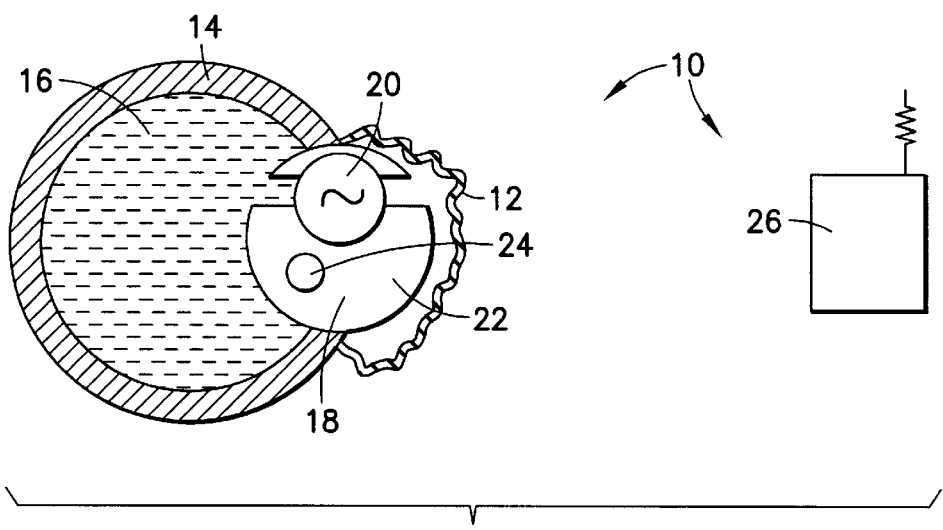
FIG. 1 is a schematic section view of a first embodiment of an intragastric balloon device according to the invention configured prior to actuation.

Turning now to FIG. 1, a first embodiment of an intragastric balloon device 10 according to the invention is shown. The balloon device 10 includes a flexible bladder 12, a relatively rigid reservoir 14 coupled to the bladder and adapted to hold a bladder inflation fluid (liquid or gas) 16, and an inflation/deflation system 18 adapted to move or permit movement of the fluid from the reservoir and into the bladder. The intragastric balloon device is sized such that it may be inserted, in its entirety, into the stomach of a patient through the esophagus. The device is preferably retained in the stomach by its size and shape, which prevent the device from being passed, without physician intervention, by the valves at the entrance and exit of the stomach.

Figure 2:
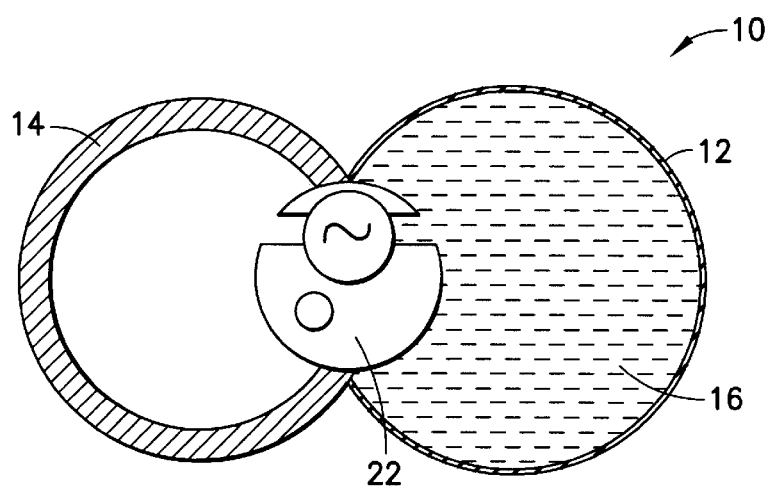
FIG. 2 is a schematic section view of the first embodiment of an intragastric balloon device according to the invention configured after actuation.

According to the invention, various inflation systems may be used to move or permit movement of the fluid. According to the first embodiment, the inflation system 18 includes a pump 20 adapted to transfer fluid 16 from the reservoir into the bladder 12 to fill the bladder (as shown in FIG. 2), and a control system 22 adapted to control, preferably automatically, operation of the pump 20. The control system 22 may include a timer or one or more sensors and be activated by a combination of one or more of a schedule of the timer, a sensed temperature of the stomach, a sensed pressure in the stomach, a sensed mechanical stress in the stomach, or another sensed condition. Upon activation. the control system 22 signs power to the pump 20 from the power source of the device, e.g., one or more batteries 24. In addition, the control system 22 can signal the pump 20 to work in reverse in order to return the fluid into the reservoir 14 thereby collapsing the bladder 12 and decreasing the size of the intragastric balloon device or, where a resilient bladder 12 is used, to simply open a valve to permit the return of the fluid.

The batteries 24 of the device are preferably primary cells which are preferably adapted to power the device for the duration of the treatment period. Alternatively, the batteries 24 may be rechargeable and may be recharged through the skin by means of external (outside the body) and internal (within the device) coils. charging of the batteries may also be performed by radio frequency from an external transmitter. Alternatively, the batteries may be recharged or replaced during an endoscopic procedure.

According to another preferred, though optional, aspect of the invention, the control system 22 is preferably reprogrammable and/or instantly operable via an external transmitter 26 operable by the patient (FIG. 1). As such, patient discomfort can be alleviated without reliance on sensed conditions by the control system 22.

The above described device, with the pump 20 used to pump fluid from the reservoir 14 into the bladder 12, permits up to a doubling of the volume of the device without having any compression of the fluid. Alternatively, the pump can compress a gas into the reservoir. Then, the gas can be expanded through the pump or a valve to inflate the bladder. This design permits a greater than two to one ratio of volume, but requires compressing the gas which has increased energy requirements. As such, the pump motor and batteries would need to be relatively larger.

In yet another variation, the fluid is a gas, such as dichlorodifluoroethane, which is liquified in the reservoir by the compressive forces of the pump. The use of such a fluid allows the volume of the reservoir to be reduced and reduces the energy requirements because the pump only has to pump against the constant saturation pressure of the condensing fluid in order to compress the fluid. This is in contrast to the compression of a non-condensing gas in which the pressure continues to rise as the gas becomes more compressed, and which requires greater energy from the pump than in the case of the condensing fluid.

In addition, if the bladder is elastic, it will require less energy to empty back into the reservoir. However, if the bladder is non-elastic it will require less energy to fill. Where an elastic balloon is utilized, a preferred material includes styrene-isobutylene-styrene, which is described in detail in U.S. Pat. No. 5,741,331 to Pinchuk.

Figure 3:
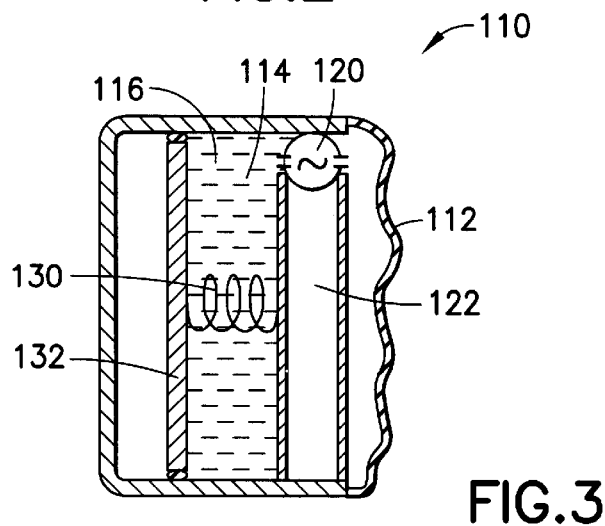
FIG. 3 is a schematic section view of a second embodiment of an intragastric balloon device according to the invention configured prior to actuation.
Figure 4:
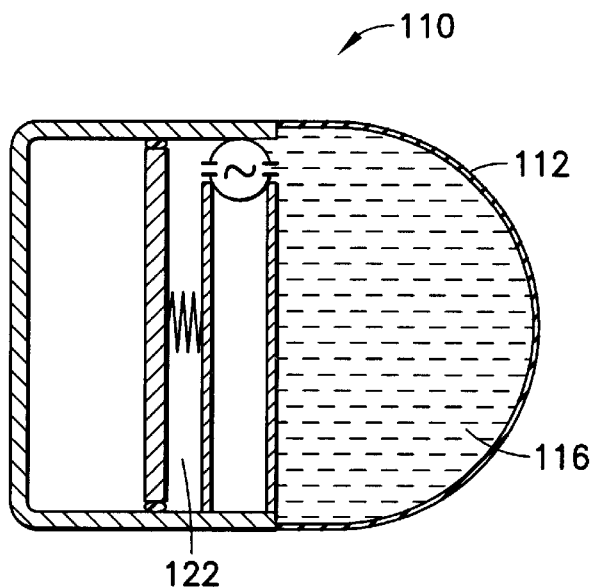
FIG. 4 is a schematic section view of the second embodiment of an intragastric balloon device according to the invention configured after actuation.

Turning now to FIG. 3, according to a second embodiment of an intragastric balloon device 110, the energy requirements of the pump 120 can be reduced by adding a spring element 130 which tends to force a sealed piston 132 away from the pump and draw fluid 116 into the reservoir 114. When it is necessary or desired to fill the bladder, the pump 120 is operated by the control system 122 to move the fluid 116 from the reservoir 114 and into the bladder 112 (FIG. 4). As an alternative to the spring and piston mechanism, the reservoir may include an expanding bellows (not shown) which exerts suction toward the pump.

Figure 5:
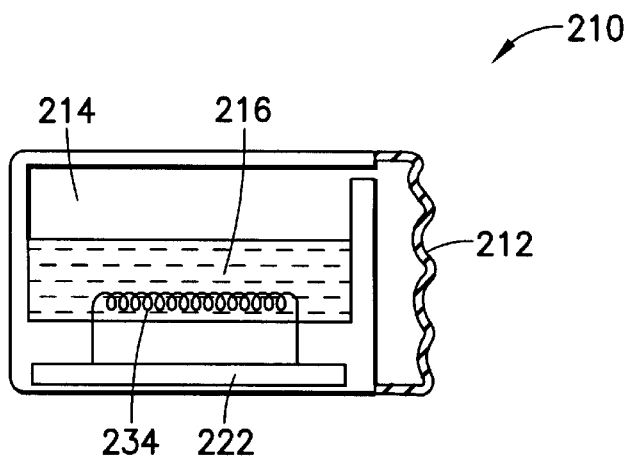
FIG. 5 is a schematic section view of a third embodiment of an intragastric balloon device according to the invention configured prior to actuation.
Figure 6:
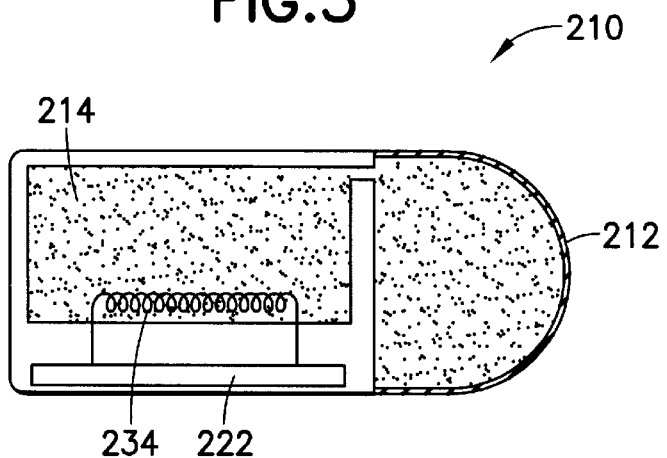
FIG. 6 is a schematic section view of the third embodiment of an intragastric balloon device according to the invention configured after actuation.

Referring now to FIG. 5, according to a third embodiment of an intragastric balloon device 210, the bladder 212 may be filled by boiling a fluid 216 located in the reservoir 214. To that end, a heating element 234 is provided in the reservoir 214 and controlled by the control system 222. The reservoir 214 is preferably a relatively poor heat conductor. When the heating element 234 is activated, the fluid 216 is heated and boils, and a gas is released into the bladder 212 to inflate the bladder (FIG. 6). Then, when the gas cools and condenses, the bladder contracts, and the device resumes the configuration shown in FIG. 5. The bladder 212 is preferably a relatively good thermal insulator so that deflation occurs relatively slowly and so that the inflated bladder 212 does not cause heat damage to the stomach and surrounding organs. In this embodiment, the bladder 212 and reservoir 214 can be an integral structure, as there is no need for a valve or pump therebetween.

Figure 7:
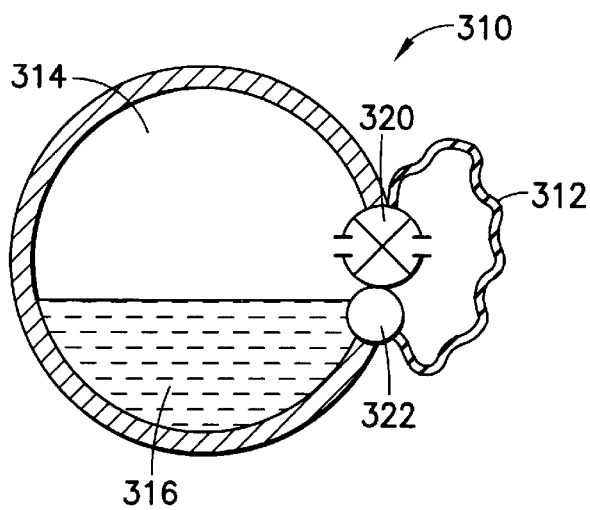
FIG. 7 is a schematic section view of a fourth embodiment of an intragastric balloon device according to the invention configured prior to actuation.

Turning now to FIG. 7, in a fourth embodiment, similar to the third embodiment, the reservoir 314 of the intragastric balloon device 310 is thermally conductive, while the bladder 312 is thermally insulative. A valve 320 is provided between the bladder 312 and the reservoir 314. The fluid 316 is chosen to boil at a temperature between just slightly above body temperature and approximately 140° F. (the temperature of a hot drink such as tea or coffee). No heating element is provided within the device.

Figure 8:
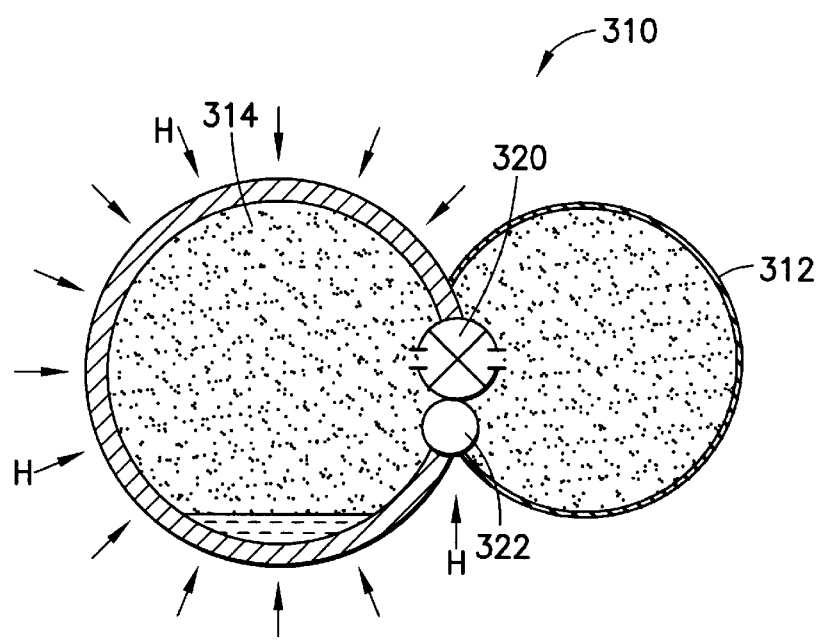
FIG. 8 is a schematic section view of the fourth embodiment of an intragastric balloon device according to the invention configured after actuation.

Referring to FIG. 8, when the patient drinks a hot liquid which is at a temperature at which the fluid 316 boils, the heat H from the liquid heats the reservoir 314 and the fluid 316 within, causing the fluid to boil into a gas, pass through the valve 320, and expand to fill the bladder 312 (FIG. 8). The bladder 312 remains inflated until the heat of the expanded gas conducts through the bladder, causing the gas to condense and the bladder to contract.

Optionally, a control system 322 may be configured to sense the temperature of the contents of the stomach cavity, and upon sensing a predetermined temperature may open the valve for a timed period to permit the inflation gas to enter the bladder, then close the valve to retain the gas therein, and then re-open the valve to allow the condensed fluid to return to the reservoir. The return of the fluid may be effected by gravity, by compression of the bladder about the fluid, or with a pump.

Alternatively, the valve 320 may consist of two fluid paths: a one-way valve that allows the gas to pass quickly from the reservoir into the bladder, and a restricted return path (with or without a one-way valve) to allow the condensing fluid to return to the reservoir. The return of the fluid may then be aided by gravity, by capillary action (by a very small tube wetted by the fluid or by a tube lined with a wicking material), or by an elasticity of the bladder that urges the fluid to return to the reservoir.

Figure 9:
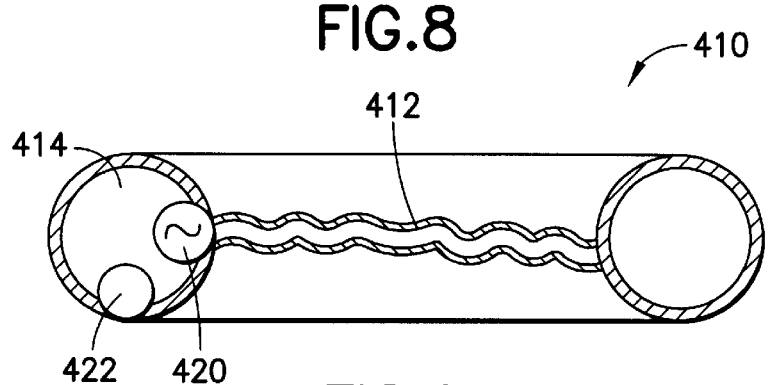
FIG. 9 is a schematic section view of the fifth embodiment of an intragastric balloon device also configured prior to actuation.
Figure 10:
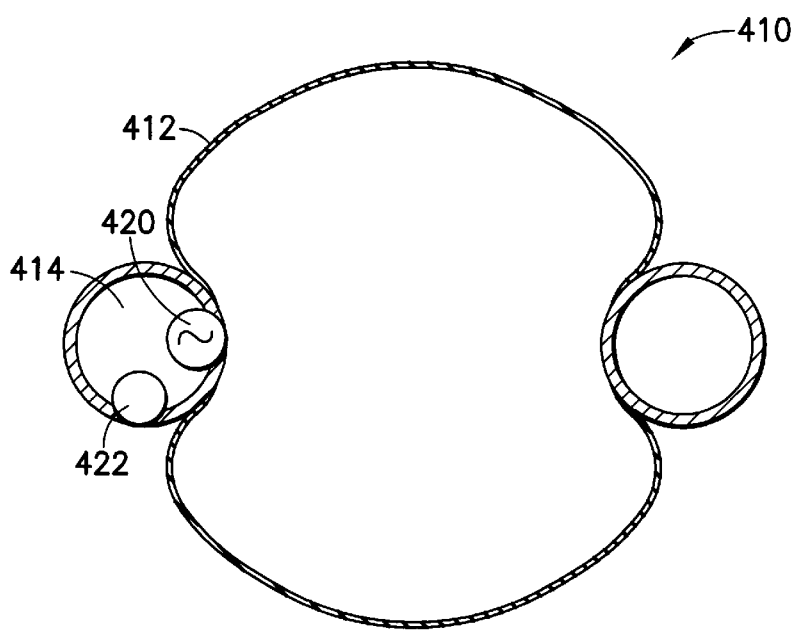
FIG. 10 is a schematic section view of the fifth embodiment of an intragastric balloon device according to the invention configured after actuation.

The above described embodiments may be provided in numerous shapes. For example, referring now to FIGS. 9 and 10, the deflated state of the reservoir 414 of the intragastric balloon device 410 may be substantially toroidal, and the bladder 412 may generally form a two-ply membrane across the center of the toroidal reservoir. The reservoir 414 houses the pump 420 and the control system 422. When, by whichever of the above described mechanisms, the bladder 412 is filled and expanded, the intragastric balloon device is provided with a substantially spherical shape. Of course, the intragastric balloon device may be provided in other shapes. For example, the reservoir may be substantially disk shaped with the bladder forming a membrane on at least one side of the disk. Then, when the bladder is expanded, the device forms either a generally hemispherical shape or spherical shape.

Figure 11:
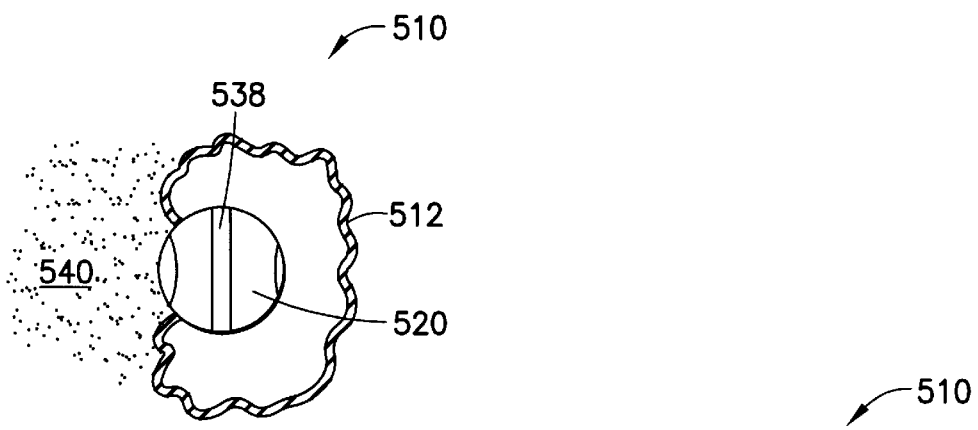
FIG. 11 is a schematic section view of the sixth embodiment of an intragastric balloon device also configured prior to actuation.
Figure 12:
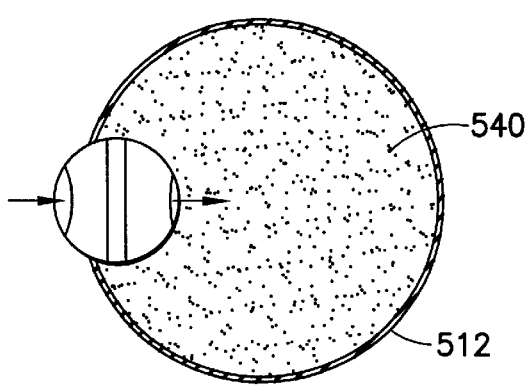
FIG. 12 is a schematic section view of the sixth embodiment of an intragastric balloon device according to the invention configured after actuation.

It is not necessary to include a reservoir, as fluid or gas in the stomach may be used to inflate the bladder. Turning now to FIG. 11, an intragastric balloon device 510 including a pump 520 coupled to a bladder 512 is shown. The pump 520, upon signal by a control system (not shown), pumps stomach gas and fluid 540 into the bladder to inflate the bladder into a balloon (FIG. 12). The pump 520 is preferably provided with a filter 538 which limits or precludes food particles or bacteria from being introduced into the bladder 512.

The above described embodiments of an intragastric balloon device permit repeated variation of the size and volume of the device within the stomach cavity. In addition, each embodiment provides a self-contained device which is operable entirely within the stomach. As such, the intragastric balloon devices of the invention prevent balloon accommodation by the stomach.

There have been described and illustrated herein several embodiments of an intragastric balloon device. While particular embodiments of the invention have been described, it is not intended that the invention be limited thereto, as it is intended that the invention be as broad in scope as the art will allow and that the specification be read likewise. Thus, while particular relative sizes of the reservoir and bladder have been shown in the schematic drawings, it will be appreciated that the relative sizes of elements in the drawings are not meant to be representative of actual relative element size. In addition, while particular relative shapes of the elements have been disclosed, it will be understood that other shapes can be used. Also, while the balloon device is shown configurable between two sizes, with the bladder substantially empty of fluid and substantially full of fluid, it will be appreciated that the pump may be operated to cause the device to assume additional intermediate sizes. It will therefore be appreciated by those skilled in the art that yet other modifications could be made to the provided invention without deviating from its spirit and scope as claimed.

What is claimed is:

1. An intragastric balloon device for insertion into a stomach cavity in a body of a patient, comprising:

a) a flexible bladder;

b) a relatively rigid reservoir coupled to the bladder and adapted to hold an inflation fluid; and c) an inflation system adapted to move or permit movement of the fluid from said reservoir and into the bladder, wherein said bladder, said reservoir, and said inflation system are together sized to be positioned, in their entireties, within the stomach cavity.

2. An intragastric balloon device according to claim 1, wherein:

said inflation system includes a pump.

3. An intragastric balloon device according to claim 1, wherein:

said inflation system also includes a valve.

4. An intragastric balloon device according to claim 1, wherein:

said inflation system includes a heating element.

5. An intragastric balloon device according to claim 1, wherein:

said inflation system is battery powered.

6. An intragastric balloon device according to claim 1, further comprising:

d) a control system adapted to automatically activate the inflation system.

7. An intragastric balloon device according to claim 6, wherein:

said control system is programmed to activate by at least one of a timer, a sensed temperature of the stomach, a sensed pressure in the stomach, and a sensed mechanical stress in the stomach.

8. An intragastric balloon device according to claim 6, wherein:

said control system is programmable, and reprogrammable via a transmitter external of the body of the patient.

9. An intragastric balloon device according to claim 6, wherein:

said control system is battery-powered.

10. An intragastric balloon device according to claim 1, further comprising:
d) a control system adapted to activate said inflation system; and
e) means external of the body of the patient for operating said control system.

11. An intragastric balloon device according to claim 1, wherein:
said bladder is elastic.

12. An intragastric balloon device according to claim 2, wherein:
said inflation system is adapted to move or permit movement of the fluid from said bladder back into said reservoir.

13. An intragastric balloon device according to claim 12, wherein:
said reservoir includes means for facilitating movement of said fluid back into said reservoir.

14. An intragastric balloon device according to claim 13, wherein:
said means for facilitating movement includes a piston, and a spring forcing said piston away from said pump.

15. An intragastric balloon device according to claim 1, wherein:
said reservoir is thermally conductive and said bladder is thermally insulative relative to said reservoir.

16. An intragastric balloon device for insertion into a stomach cavity in a body of a patient, comprising:
a) a flexible bladder;
b) a reservoir coupled to the bladder and adapted to hold an inflation fluid;
c) a valve between said bladder and said reservoir; and
d) an inflation fluid within said reservoir,
wherein when said inflation fluid is heated to a temperature substantially above 98.6° F. said inflation fluid boils and expands through said valve to inflate said bladder,
said bladder, said reservoir, and said valve are together sized to be positioned, in their entireties, within the stomach cavity.

17. An intragastric balloon device according to claim 16, further comprising:
e) a heating element adapted to heat said inflation fluid; and
f) a control system adapted to operate said heating element.

18. An intragastric balloon device according to claim 16, wherein:
said reservoir is substantially thermally conductive relative to said bladder, and said inflation fluid is adapted to boil when said reservoir is heated by a hot liquid consumed by the patient.

19. An intragastric balloon device according to claim 16, wherein:
said inflation fluid is adapted to boil at a predetermined temperature above body temperature.

20. An intragastric balloon device for insertion into a stomach cavity in a body of a patient, the stomach cavity including at least one of a gas and a liquid fluid, food particles, and bacteria, said device comprising:
a) a flexible bladder;
b) a pump coupled to said bladder and adapted to pump fluid from the stomach cavity into said bladder to inflate said bladder; and
c) a control system to operate the pump,
said bladder, said pump and said control system together sized to be positioned, in their entireties, within the stomach cavity.

21. An intragastric balloon device according to claim 20, wherein:
said pump includes a filter which substantially prevents at least one of the food particles and the bacteria from entering said bladder when said pump pumps fluid from the stomach cavity into said bladder.

* * * * *

UNITED STATES PATENT AND TRADEMARK OFFICE
CERTIFICATE OF CORRECTION

PATENT NO. : 6,579,301 B1
DATED : June 17, 2003
INVENTOR(S) : Thomas O. Bales et al.

It is certified that error appears in the above-identified patent and that said Letters Patent is hereby corrected as shown below:

<u>Title page,</u>
Item [75], Inventors, add -- Charles S. Termin, Coral Gables, FL (US) --

Signed and Sealed this

Tenth Day of August, 2004

JON W. DUDAS
*Acting Director of the United States Patent and Trademark Office*